United States Patent
Rehil

(10) Patent No.: US 7,150,753 B2
(45) Date of Patent: Dec. 19, 2006

(54) NON-DISPOSABLE TROCAR NEEDLE AND HANDLE

(75) Inventor: Om P. Rehil, Marion, IN (US)

(73) Assignee: Om Prakash Rehil, Marion, IN (US)

(*) Notice: Subject to any disclaimer, the term of this patent is extended or adjusted under 35 U.S.C. 154(b) by 608 days.

(21) Appl. No.: 10/219,485

(22) Filed: Aug. 16, 2002

(65) Prior Publication Data

US 2004/0034370 A1 Feb. 19, 2004

(51) Int. Cl.
A61B 17/04 (2006.01)

(52) U.S. Cl. ........................ 606/144; 606/148

(58) Field of Classification Search ............... 606/139, 606/144, 145, 148, 222–225; 289/17
See application file for complete search history.

(56) References Cited

U.S. PATENT DOCUMENTS

| 3,645,222 A * | 2/1972 | Zocher ................. 112/224 |
| 4,406,237 A * | 9/1983 | Eguchi et al. ............ 606/145 |
| 4,527,564 A | 7/1985 | Eguchi et al. |
| 5,015,250 A * | 5/1991 | Foster .................. 606/148 |
| 5,059,207 A | 10/1991 | Shah |
| 5,152,769 A | 10/1992 | Baber |
| 5,320,632 A | 6/1994 | Heidmueller |
| 5,336,239 A | 8/1994 | Gimpelson |
| 5,501,688 A * | 3/1996 | Whiteside et al. ......... 606/148 |
| 5,562,685 A * | 10/1996 | Mollenauer et al. ....... 606/144 |
| 5,573,542 A * | 11/1996 | Stevens ................. 606/144 |
| 5,632,752 A | 5/1997 | Buelna |
| 6,099,538 A * | 8/2000 | Moses et al. ............ 606/144 |
| 6,723,107 B1 * | 4/2004 | Skiba et al. ............. 606/144 |

OTHER PUBLICATIONS

Journal of the Society of Laparoscopic Surgeons, Apr.-Jun. 2002, Nicola Di Lorenzo, M.D., Port-Site Closure: A New Problem, An Old Device, pp. 181-183.

* cited by examiner

Primary Examiner—Julian W. Woo

(57) ABSTRACT

A non-disposable trocar needle and handle for suturing laparoscopic and other small incisions. In one embodiment, the trocar needle has a handle and a curved needle tip which allow a surgeon, with a single twist of the handle, to pass the needle through the fascia, muscle and peritoneal layers on both sides of an incision. In another embodiment the trocar needle has a straight shaft with an eyelet defined through the sharp, pointed tip, the eyelet having a larger diameter on one end than the opposite end for better visualization laparoscopically.

5 Claims, 19 Drawing Sheets

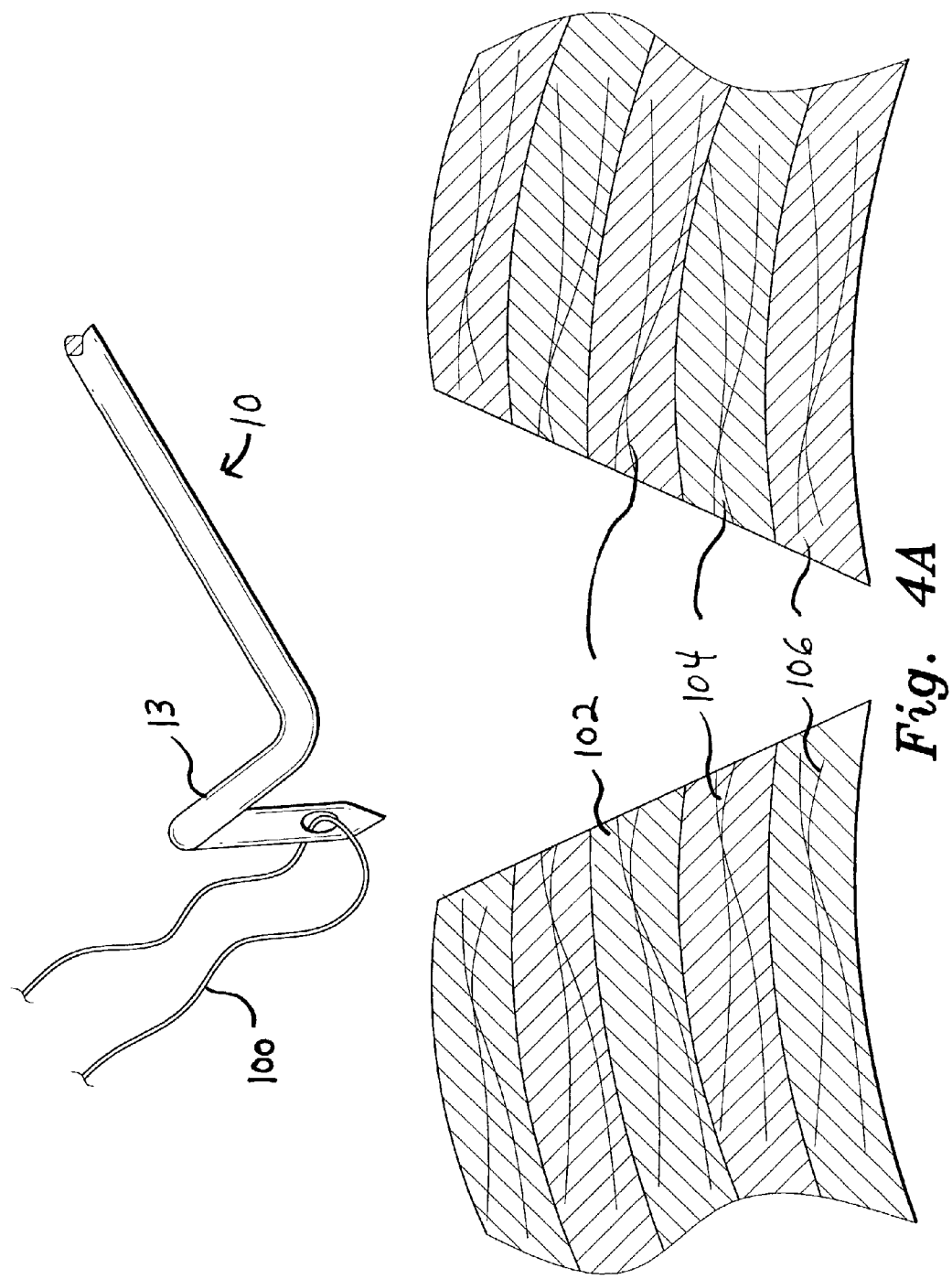

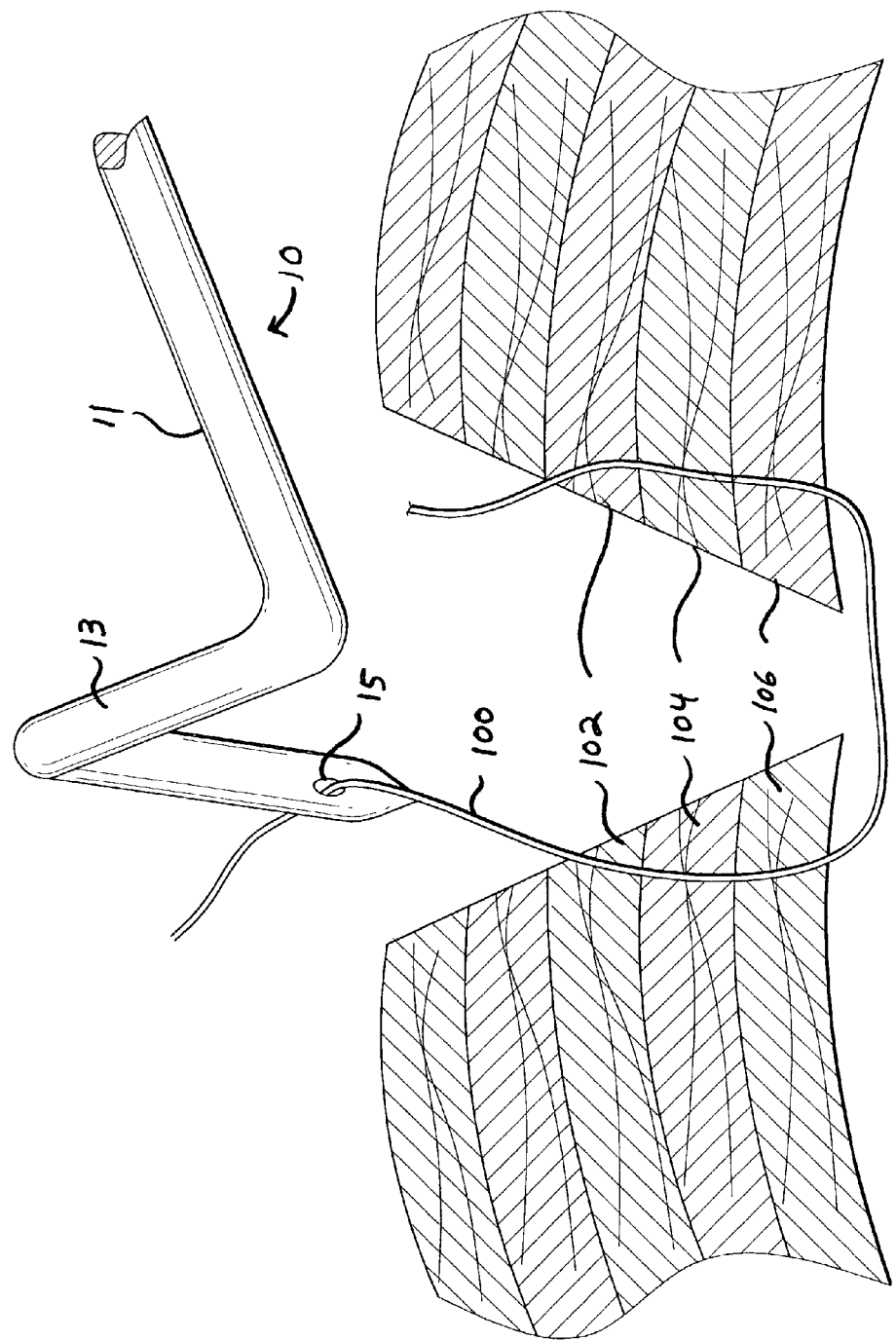

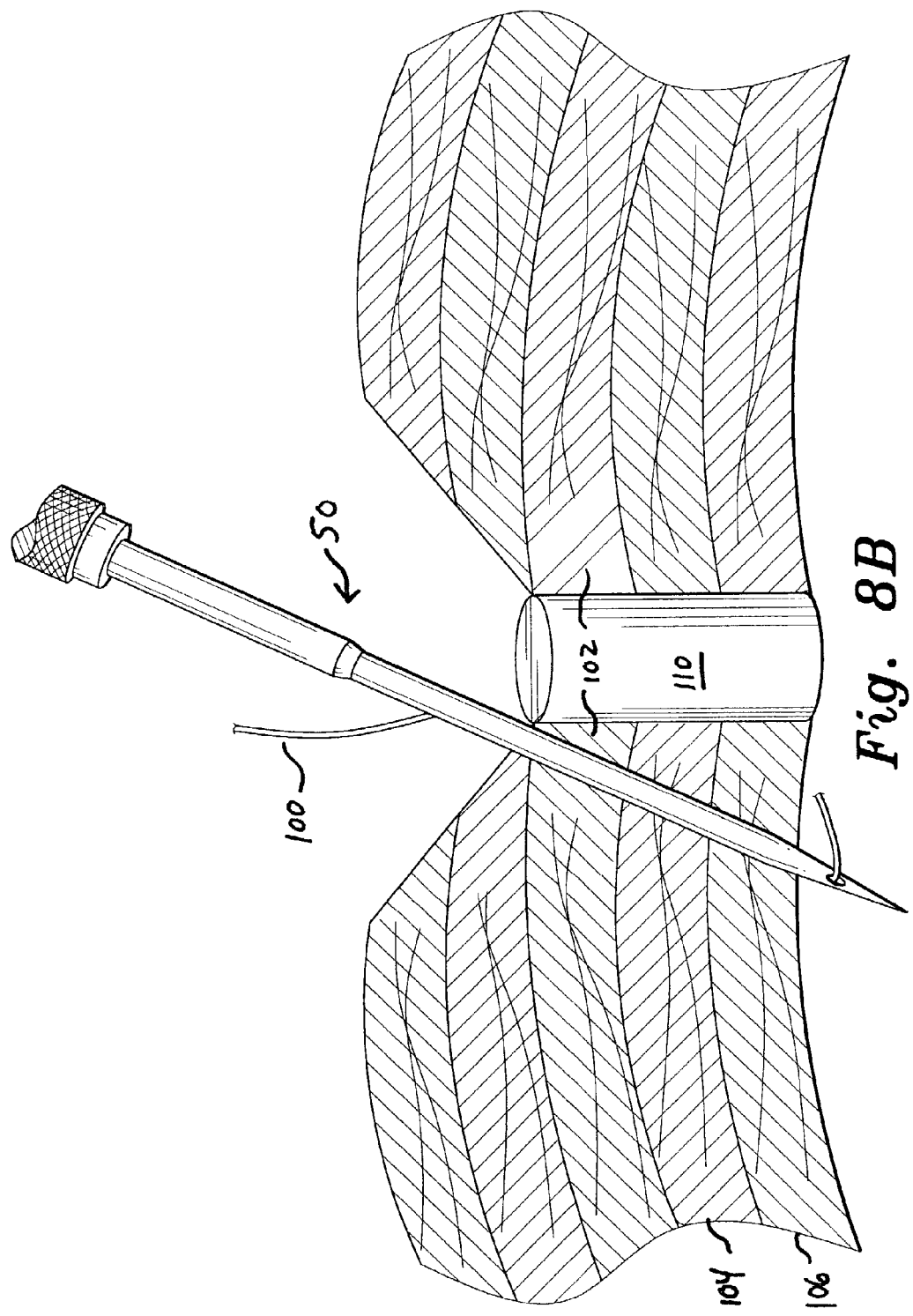

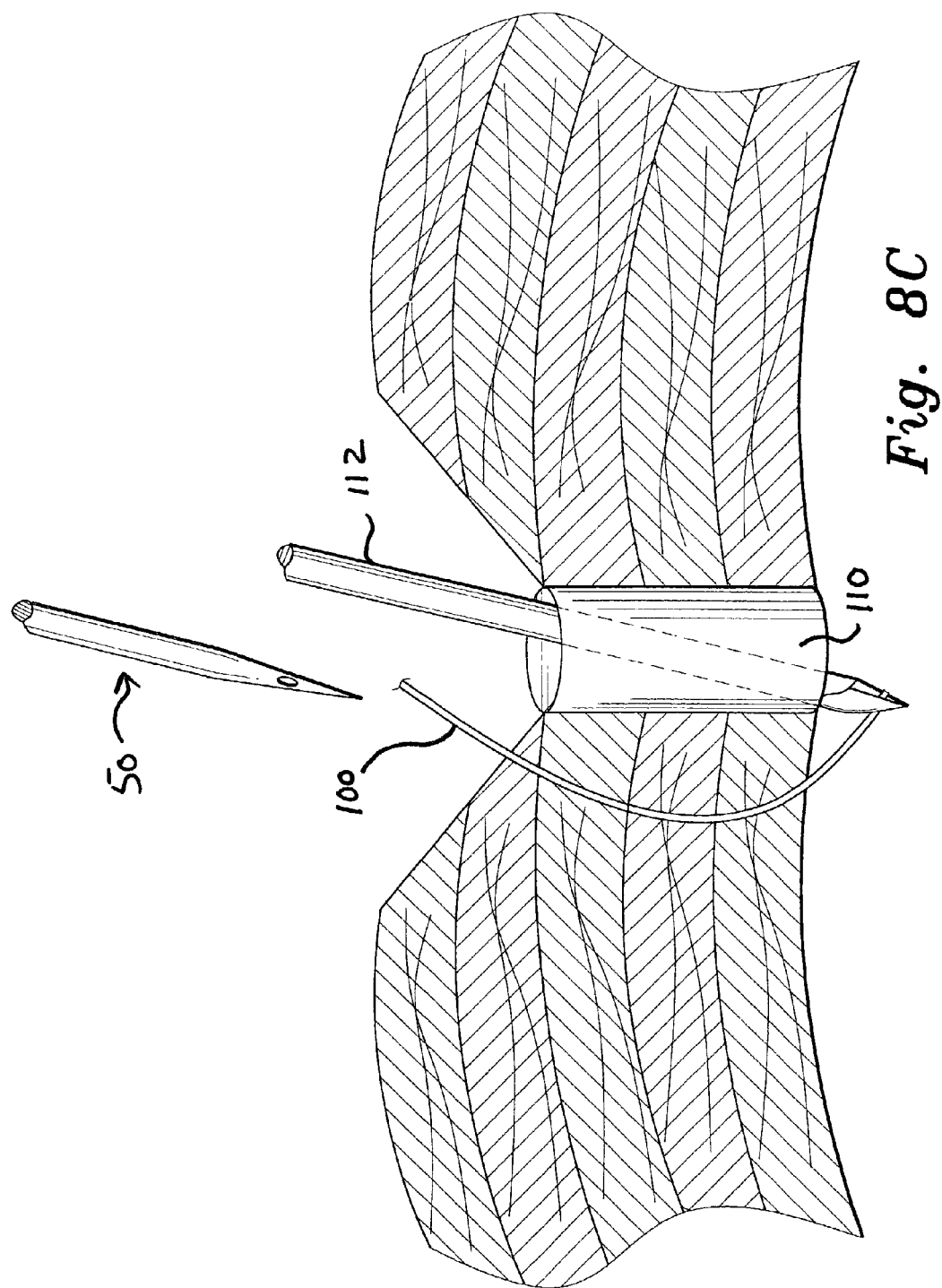

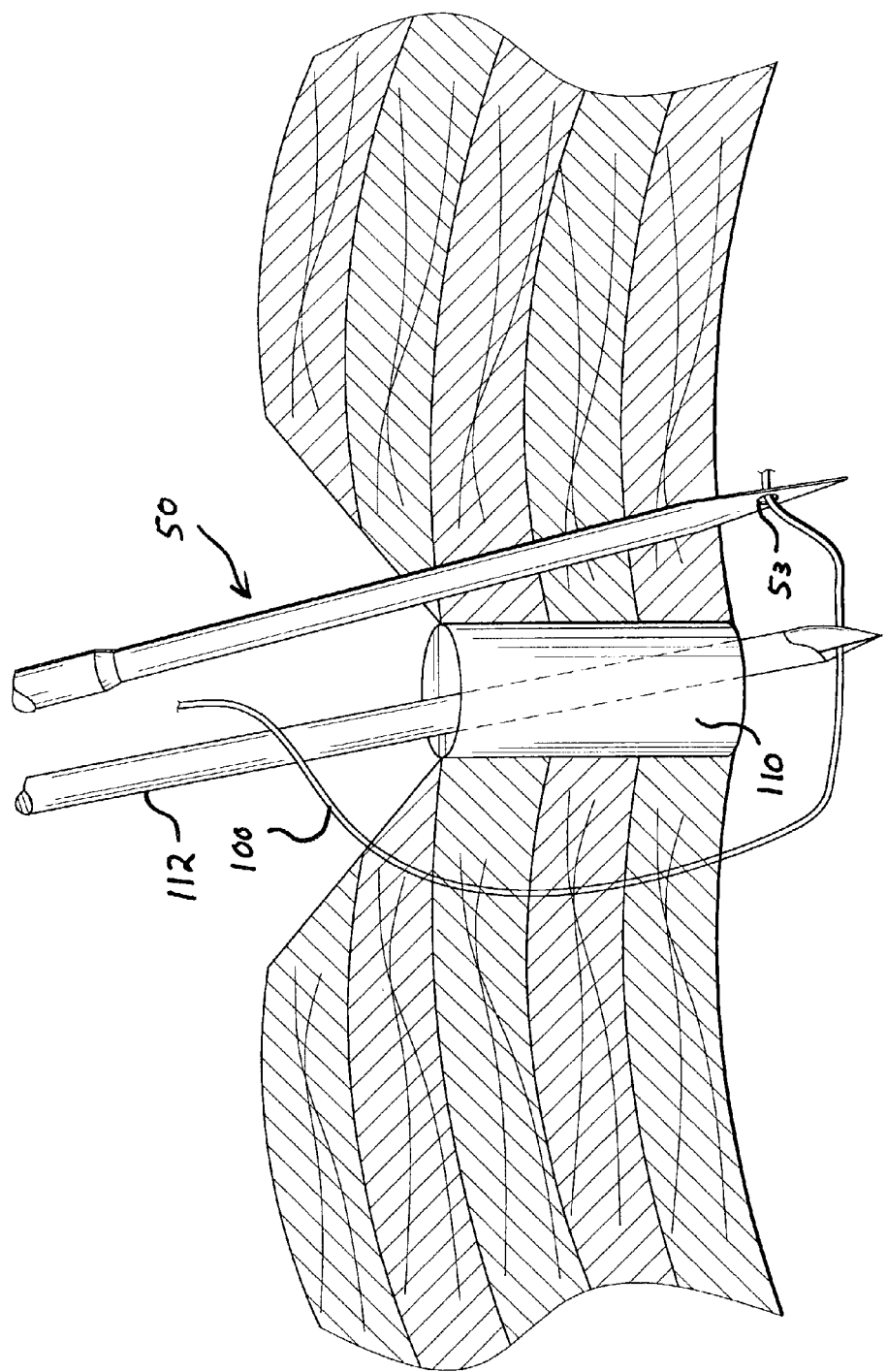

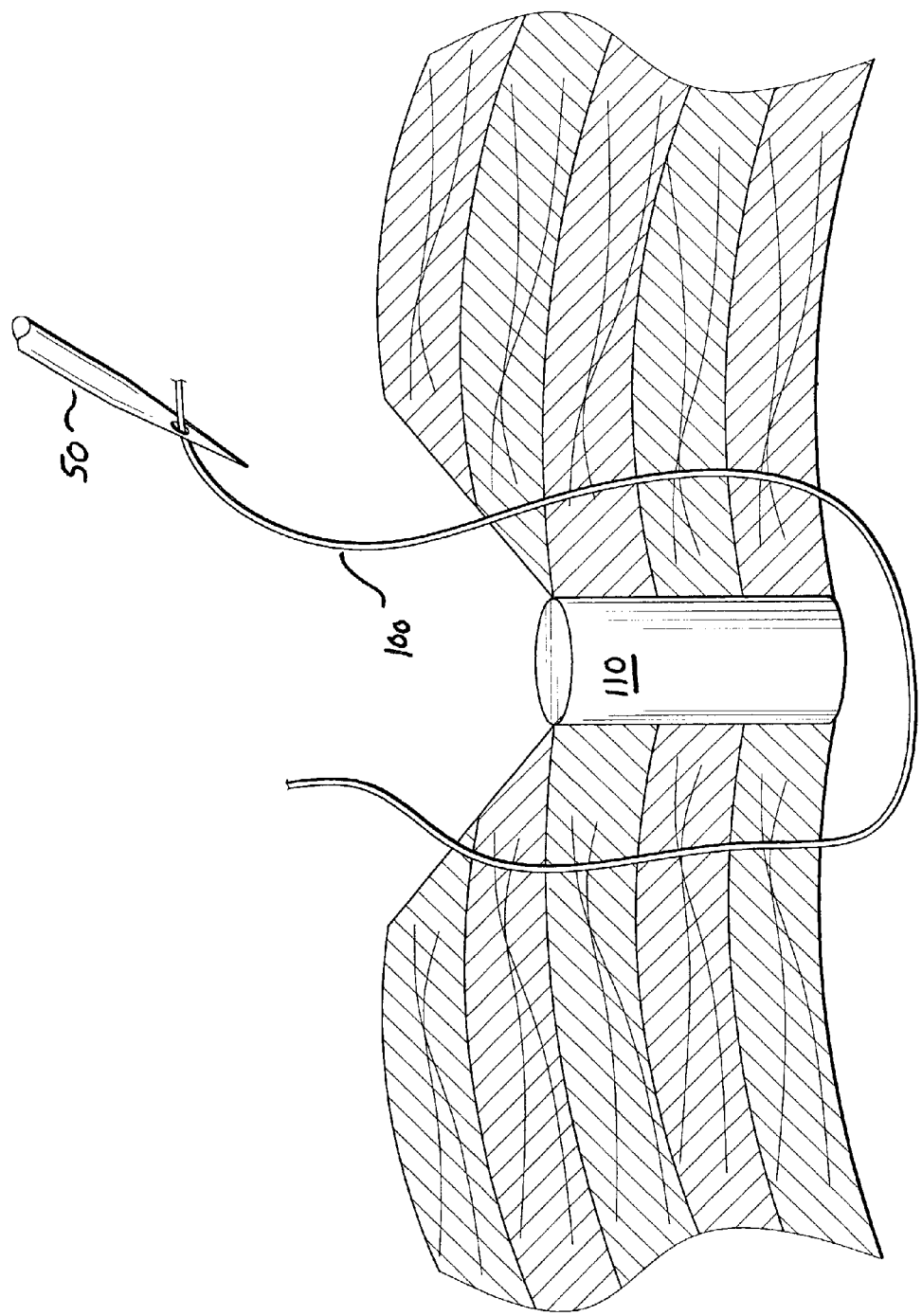

NON-DISPOSABLE TROCAR NEEDLE AND HANDLE

BACKGROUND OF THE INVENTION

1. Field of the Invention

The present invention relates to medical devices for suturing incisions and, more particularly, to a non-disposable trocar needle for suturing laparoscopic incisions and other small incisions. The preferred embodiment of the present invention incorporates both a handle and a curved needle tip which allow a surgeon, with a single twist of the wrist, to pass the needle through the fascia, muscle and peritoneal layers on both sides of an incision.

2. Description of the Related Art

Minimally invasive surgical procedures, such as laparoscopy, are performed through small incisions with specially-designed elongated surgical instruments. Such surgeries typically require puncturing through a patient's body tissue and inserting a hollow cylindrical tube, known as a cannula or sheath, through the puncture. Once the cannula is inserted, the elongated surgical instruments are then manipulated through the cannula.

Following such a procedure, the surgeon must suture the incision closed. This is often a difficult task because such incisions are typically small but deep. For example, a laparoscopic incision through the abdominal wall can be as small as four millimeters (less than one quarter of an inch) in diameter but more than twenty-five millimeters (one inch) deep. Thus, a surgeon typically is unable to get his fingers into the incision to suture in a conventional manner. Instead, a surgeon must typically pass a needle and suture through the tissue on one side of the incision and into the patients body; manipulate the needle and suture with dolphin forceps via the small incision; and then pass the needle and suture through the tissue on the other side of the incision and out of the body. Even though suturing done in this manner is difficult and time consuming, it is important that it be done well. Otherwise, the risk of a hernia through the site of the incision is increased.

Several devices have been developed for suturing incisions. U.S. Pat. No. 4,527,564, issued to Eguchi et al., U.S. Pat. No. 5,059,207, issued to Shah, U.S. Pat. No. 5,320,632, issued to Heidmueller, U.S. Pat. No. 5,336,239, issued to Gimpelson, and U.S. Pat. No. 5,632,752, issued to Buelna, show representative devices. Each of the needles or devices taught by these patents, however, has at least one drawback. Specifically, the needles taught by Eguchi et al., Shah and Gimpelson do not have a handle, or at least a handle that is easily grasped, and therefore each of these needles is difficult to grip and manipulate. Additionally, due to the shapes and sizes of the needles, it is difficult for a surgeon to pass the needles through both sides of an incision in one motion. Likewise the device taught by Buelna, which consists essentially of a handle with a retractable u-shaped needle that curves in the plane of the handle, cannot be passed through both sides of an incision in one motion. Furthermore, both Buelna and Heidmueller teach devices with moving parts which makes sterilization of the instruments more difficult, makes manufacture of the instrument more expensive, and makes use of the instruments more complex.

Additionally, U.S. Pat. No. 5,152,769 to Baber teaches a laparoscopic suturing device for suturing internal incisions. The device consists of an outer barrel and an inner barrel which are inserted through a cannula. A hollowed curved needle is attached to the outer barrel and an open loop grasping means is attached to the inner barrel. The needle and grasping means are manipulated to suture an internal incision such as one of an internal organ within the abdominal cavity.

Similar to the present invention, Baber teaches a needle that is curved in an arc and is perpendicular to its point of attachment. However, Baber differs in its complexity and structure from the present invention. Baber teaches a hollowed needle that is attached to a cylindrical barrel with a suture material fed through the barrel, into the hollowed needle and out of a single opening on the interior aspect of the needle. On the other hand, the present invention teaches a simple and easy-to-use device consisting of a solid needle with a transverse eyelet and an elongated shaft that is attached to an easily grasped knurled handle. Furthermore, in addition to its structural differences from the present invention, the device taught by the Baber patent is designed for use through a cannula and, therefore, is not suited for closing an incision of the outer layers.

As described in the article "Port-Site Closure:A New Problem, An Old Device", Di Lorenzo et al., *JSLS* 6 (2): 181–183, published April, 2002, a device known as a Deschamps needle has been used for "en masse" ligature of pedicles, and consists of a needle with a curved tip and a handle attached to the shaft of the needle. Although the Deschamps needle bears some resemblance to the present invention, its differences are significant. First, the tip of the Deschamps needle curves extends in a helical curve from the shaft, so that the entrance hole and the exit hole are offset from each other for diagonal stitching, which makes the device unsuitable for small laparoscopic incisions, which may be only one quarter of an inch in length. In contrast, the tip of the present invention curves in a single plane that is perpendicular to the shaft thereby allowing suturing by simply rotating the handle. Importantly, minimizing the required movement of a surgical instrument enhances its ease-of-use and reduces the likelihood of error. The second difference is that the arc of the Deschamps tip is shallow and therefore only allows the tip to pass through a thin layer of tissue. By contrast, the arc of the present invention is deep thereby allowing the surgeon to pass the tip and suture through multiple layers of tissue on both sides of an incision, including relatively thick layers of fascia and muscle. This is significant because increasing the amount of tissue within the suture reduces the risk of hernia.

Consequently, none of the above inventions and patents, taken either singularly or in combination, is seen to describe the instant invention as claimed. Thus a non-disposable trocar needle with a handle solving the aforementioned problems is desired.

SUMMARY OF THE INVENTION

The present invention is a non-disposable trocar needle and handle for suturing laparoscopic and other small incisions. In one embodiment, the trocar needle incorporates an ergonomic handle and a curved needle tip which allows a surgeon to pass the needle, with one twist of the handle, through the fascia, muscle and peritoneal layers on both sides of a small incision. In another embodiment, the trocar needle comprises a handle and a straight shaft with a sharp, pointed tip end having an eyelet extending transversely through the shaft, in which the diameter of the eyelet opening is greater on one side of the needle than on the opposite side of the needle, which makes visualization of the needle and suture easier through a laparoscope.

Accordingly, it is an object of the invention to provide a suturing device that is easy to handle and manipulate, thereby allowing surgeons to close small incisions with less effort and less time.

It is another object of the invention to provide a suturing device that allows surgeons to suture laparoscopic incisions in a more effective manner thereby lessening the risk of a hernia.

It is a further object of the invention to provide a suturing device that does not require manipulation of the needle through a trocar, cannula, or other laparoscopic port, or the practice of a complex procedure but, instead, is simple to use.

Still another object of the invention is to provide a suturing device that is reusable, easily sterilized and maintained, and inexpensively manufactured.

These and other objects of the present invention will become readily apparent upon further review of the following specification and drawings.

BRIEF DESCRIPTION OF THE DRAWINGS

FIGS. 4A, 4B, 4C, 4D and 4E are successive diagrammatic sectional views illustrating suturing of a laparoscopic incision with the trocar needle and handle shown in FIGS. 1–3.

FIGS. 8A, 8B, 8C, 8D, 8E, 8F and 8G are successive diagrammatic sectional views illustrating suturing of a laparoscopic incision with the trocar needle and handle shown in FIGS. 5–7.

Similar reference characters denote corresponding features consistently throughout the attached drawings.

DETAILED DESCRIPTION OF THE SPECIFIC EMBODIMENTS

Figure 1:
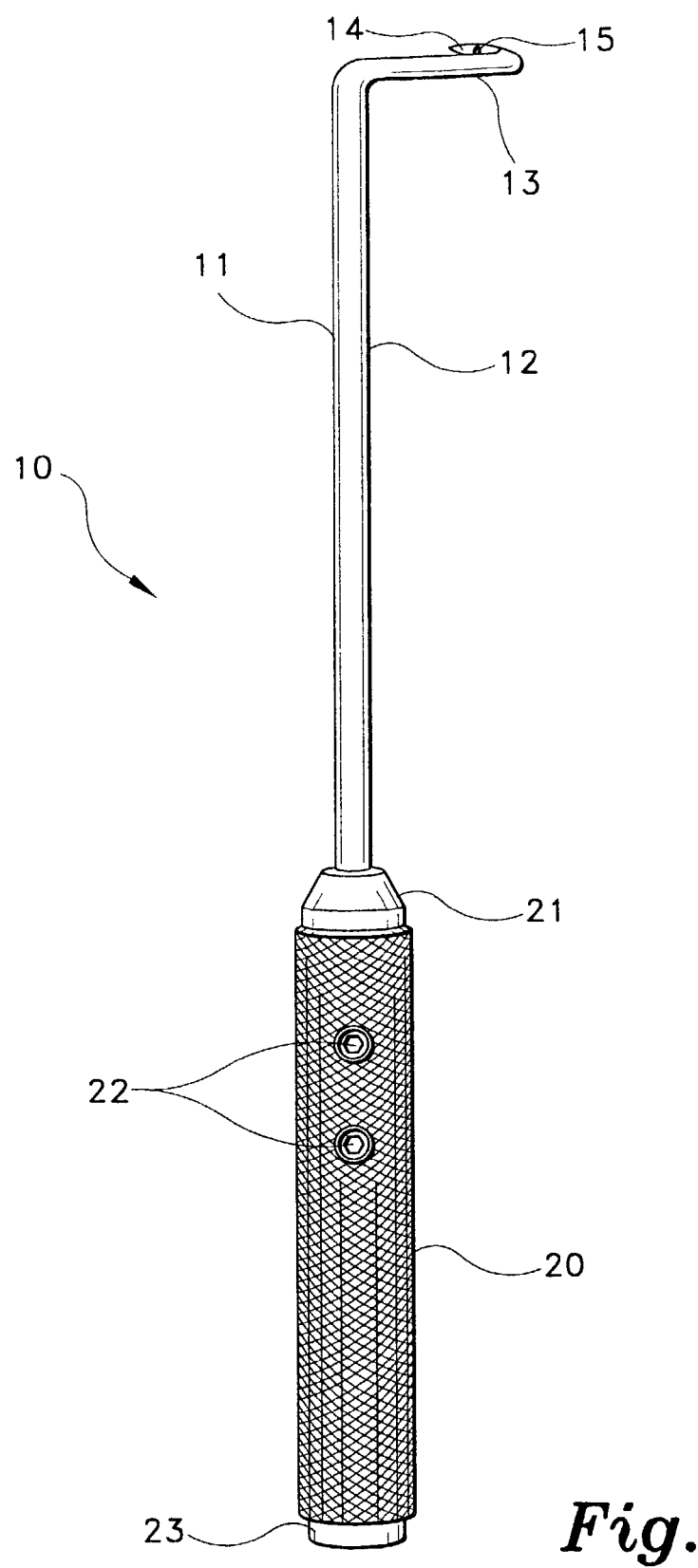
FIG. 1 is an elevation view of a first embodiment of a trocar needle and handle according to the present invention.

Referring to the drawings, FIGS. 1 through 4E illustrate a first embodiment of the present invention and FIGS. 5 through 8G illustrate an alternative embodiment of the present invention. FIG. 1 of the drawings presents an elevational view of a first embodiment of the trocar needle and handle 10 according to the present invention. It will be appreciated from the drawing that the device is comprised of two main subcomponents: a needle 11 and a handle 20. The needle 11, which extends from the proximal end 21 of the handle 20, has a shaft 12 and a tip 13. The shaft 12 is straight and is secured to the handle 20 by insertion into a bore 26 (shown in FIG. 3) defined in handle 20 and tightening two set screws 22 into the handle 20. The tip 13 of the needle 11 extends from the shaft 12 and is curved in a plane that is substantially perpendicular to the shaft 12. The end 14 of the tip 13 is formed to a sharp point. An eyelet 15 is located near the point 14 of the tip 13.

The handle is cylindrical in shape with a proximal end 21 and a distal end 23. A bore 26 (seen in FIG. 3), which is dimensioned to accommodate the shaft 12 of the needle 11, runs from the proximal end 21 toward the distal end 23. Two threaded holes 25 (shown in FIG. 3), dimensioned to accommodate two set screws 22, extend transversely from the outer surface of the handle 20 to the bore 26. The two set screws 22 are tightened in the threaded holes 25 to bear against the portion of the shaft 12 of the needle 11 that is within the bore 26. Preferably the surface of the handle 20 is knurled or otherwise patterned to provide a non-slip gripping surface.

Figure 2:
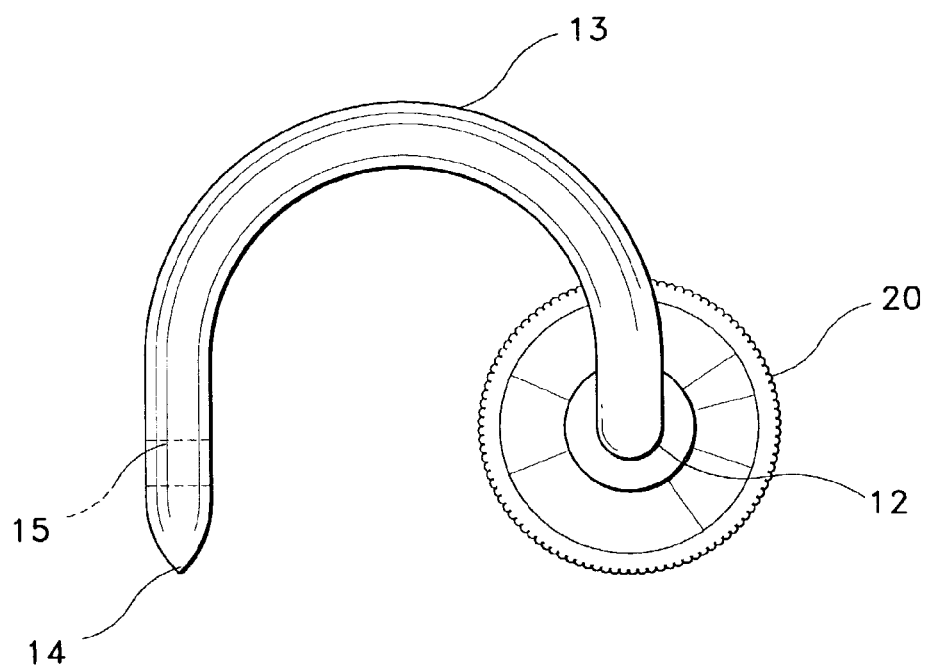
FIG. 2 is a top end view of the trocar needle and handle of FIG. 1 according to the present invention.

FIG. 2 presents a top end view of the first embodiment of the trocar needle 10. The tip 13 of the needle is curved in an arc that is perpendicular to the needle shaft 12. The eyelet 15 of the needle, shown in phantom lines, is near the point 14 of the tip 13. The shaft 12 of the needle is secured to the handle 20 via the proximal end of the handle 20. It will be noted that the curvature of the needle tip 13 describes a deep, parabolic or U-shaped arc, and that the sharp point 14 of the needle 11 extends at least to, and may extend beyond the shaft 12 so that the arc described by the tip end 13 of the needle 11 is greater than or equal to 180°.

Figure 3:
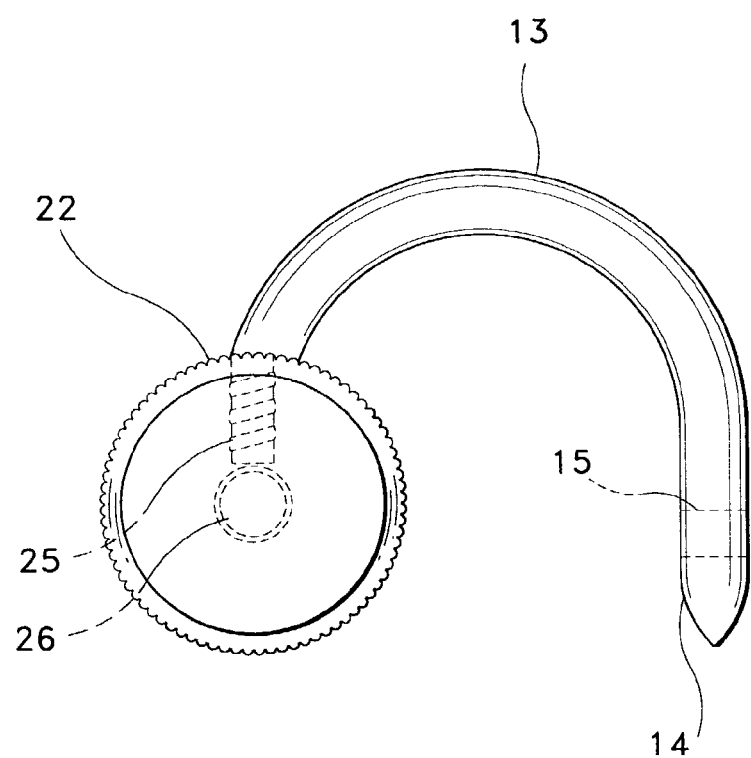
FIG. 3 is a bottom end view of trocar needle and handle of FIG. 1 according to the present invention.

FIG. 3 presents a bottom end view of the trocar needle 10. The bore 26 in the handle and the threaded holes 25 are shown in phantom lines.

Figure 4B:
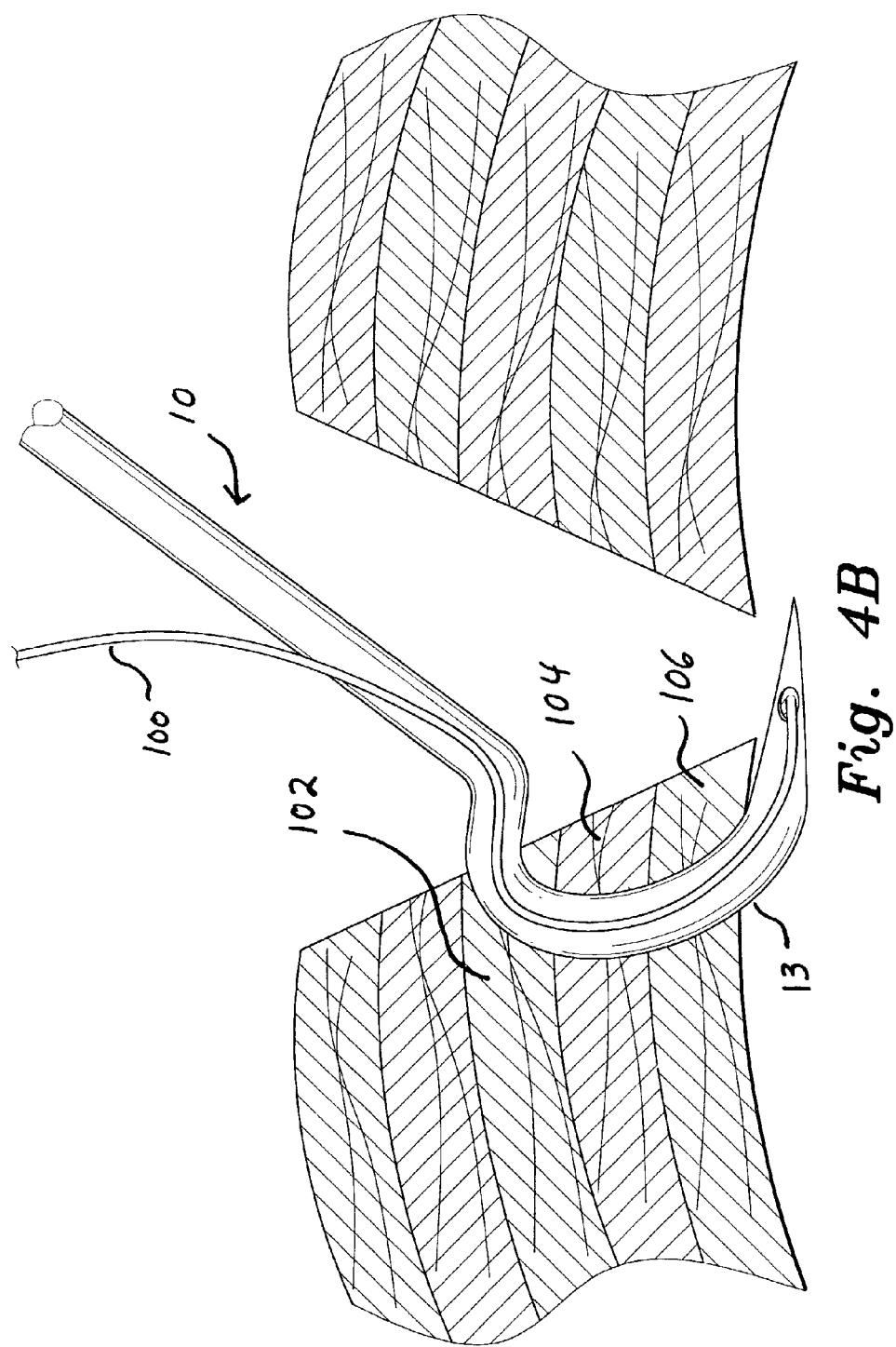
Figure 4C:
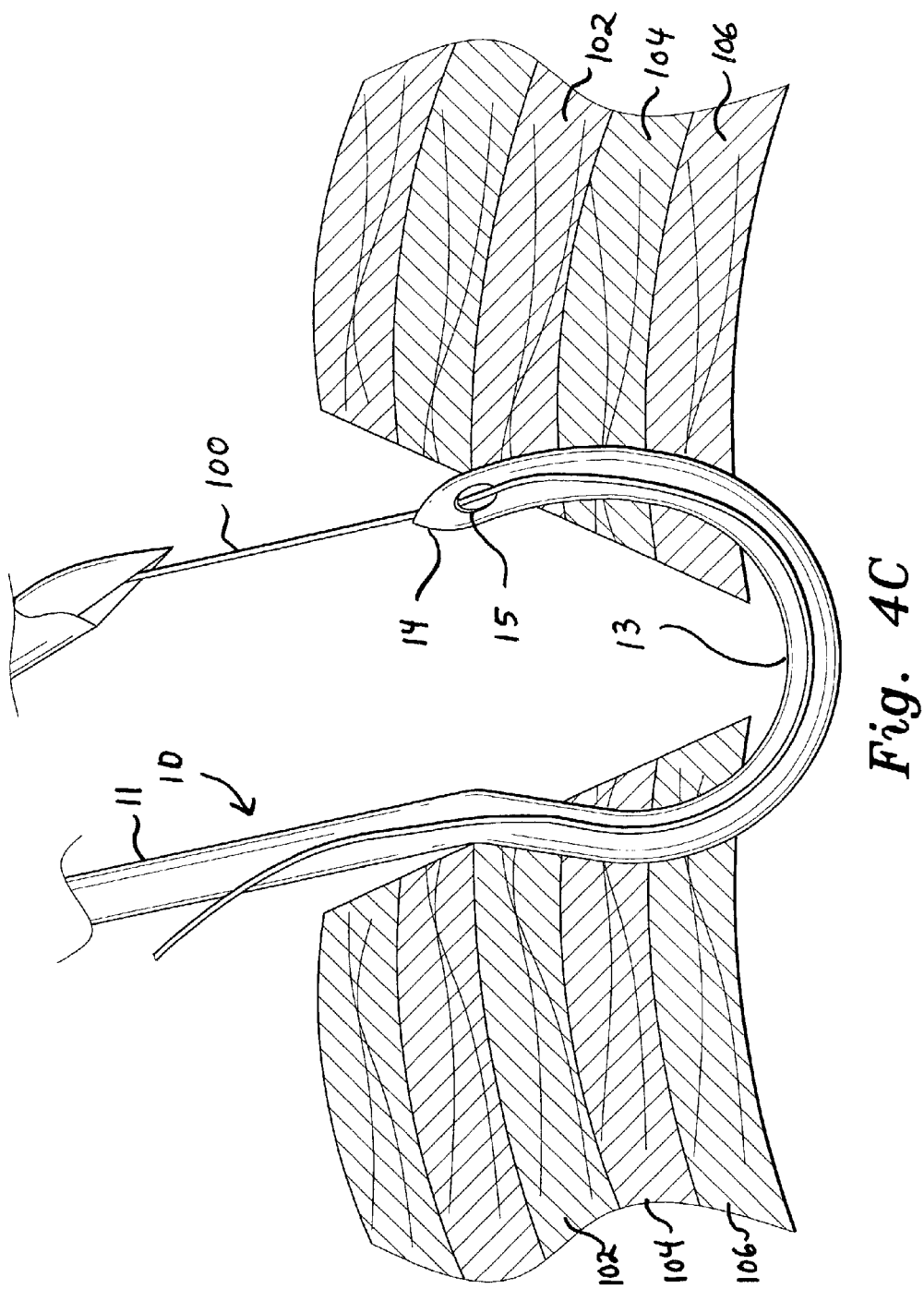
Figure 4E:
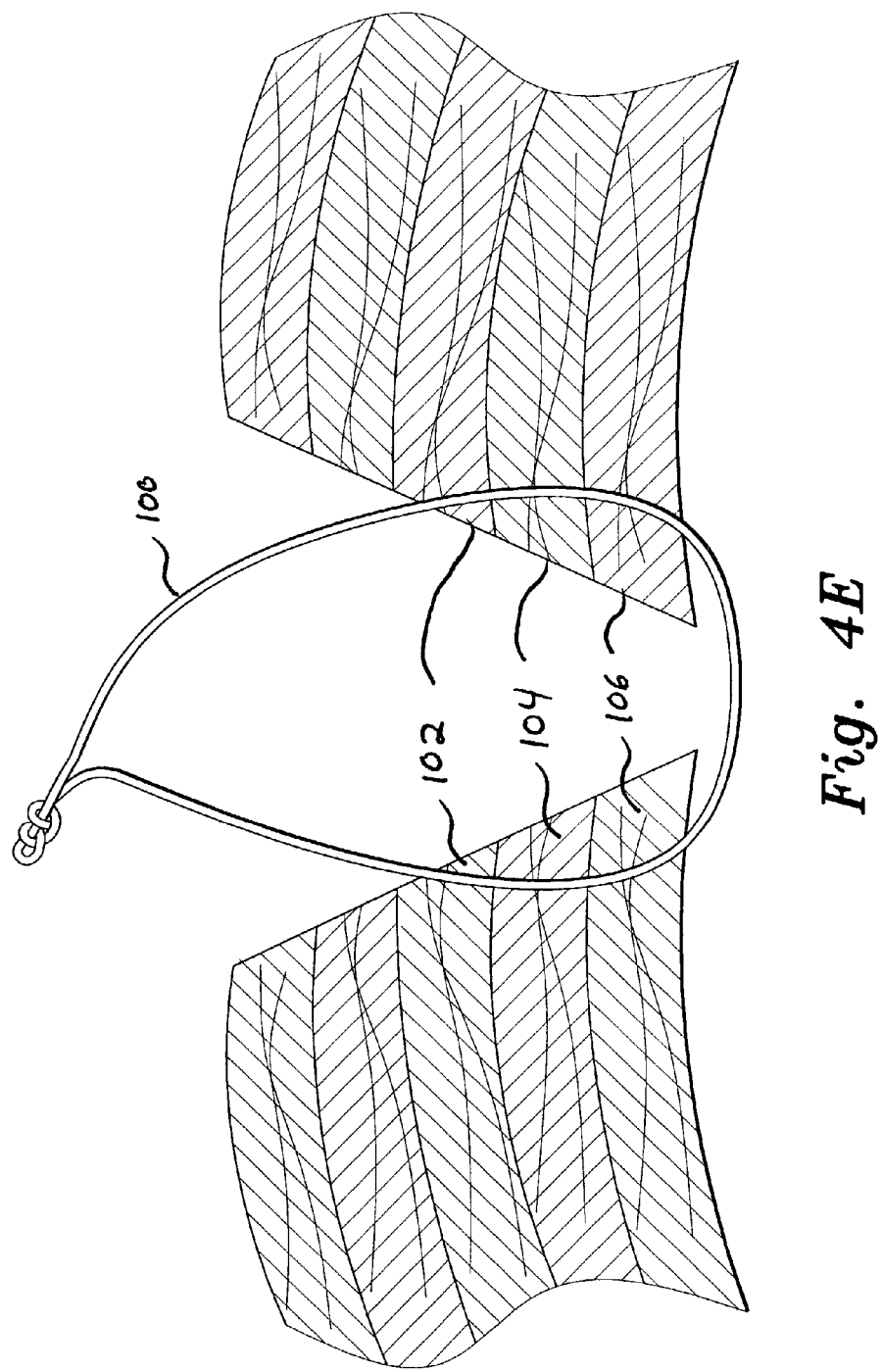

FIGS. 4A through 4E diagrammatically illustrate suturing of a laparoscopic incision with the preferred embodiment of the present invention. As shown in FIG. 4A, the needle 10 is threaded with suture 100 and positioned over the fascia layer of one side of the incision. The handle of the device is then rotated so that the tip of the needle turns downward into and pierces the tissue on one side of the incision, thereby passing through the fascia 102, muscle 104 and peritoneal 106 layers, as shown in FIG. 4B. As rotation of the handle continues, the tip 13 of the needle turns upward into and pierces the tissue on the other side of the incision, as seen in FIG. 4C. The suture 100 is then held in place, e.g., with forceps, as the needle tip 13 is withdrawn by rotating the handle in the opposite direction, as shown in FIGS. 4C and 4D. After the needle 10 is withdrawn, the suture 100 is drawn to approximate the tissue and the suture 100 is knotted (the tissue has not been shown drawn together in FIG. 4E for clarity). Once the fascia 102, muscle 104 and peritoneal 106 layers have been sutured, the dermal layers can then be sutured.

Figure 5:
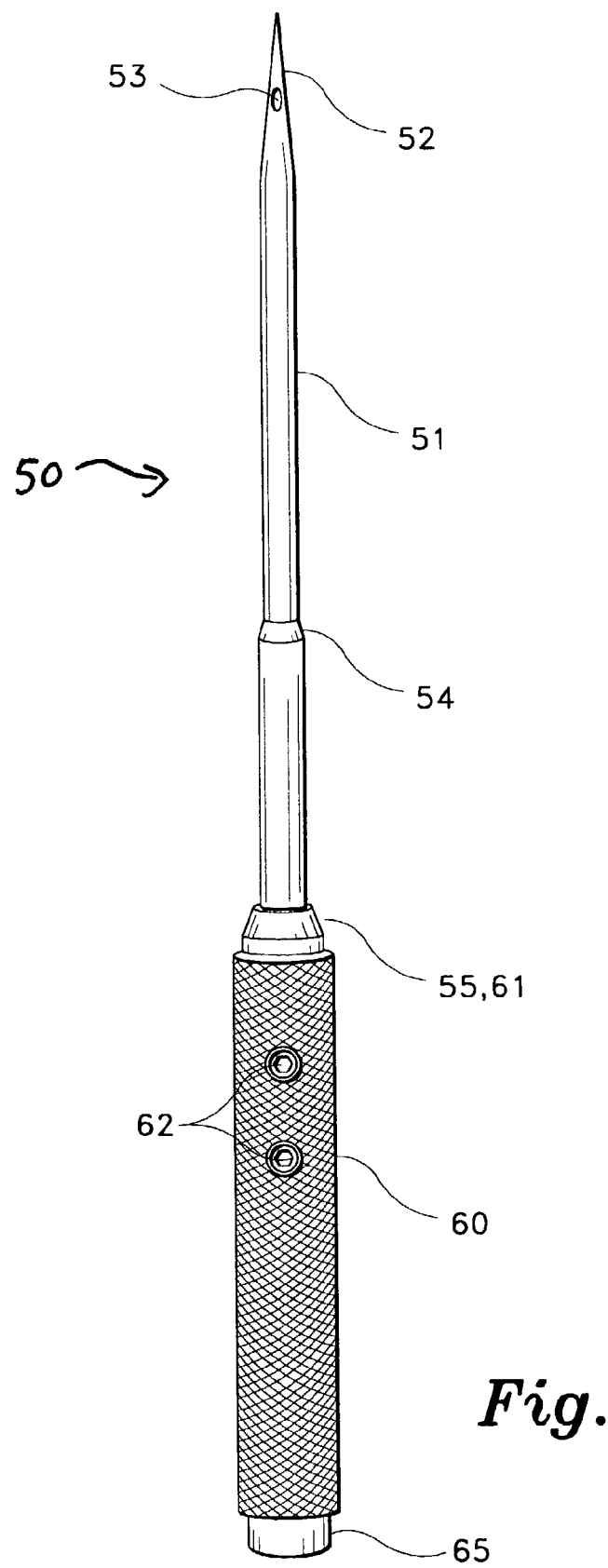
FIG. 5 is an elevational view of an alternative embodiment of a trocar needle and handle according to the present invention.

FIG. 5 presents an elevational view of an alternative embodiment of a trocar needle and handle according to the present invention, designated as 50 in the drawings. The device 50 is comprised of two main subcomponents: a needle 51 and a handle 60. The needle 51 is substantially straight and has two ends, including a tip end with a tip that is formed to a sharp point 52 and another end that is secured to the proximal end of the handle 60. Near the point 52 of the needle 51 is an eyelet 53. The needle 51 is designed with a shoulder 54 between its tip 52 and its proximal end 55. The diameter of the portion of the needle shaft 51 between the tip 52 and the shoulder 54 is less than the diameter of the needle shaft 51 between the shoulder 54 and the handle 60. The shoulder 54 acts as a safeguard against introducing the needle 51 too far into the tissue on either side of an incision. The needle 51 is secured to the handle 60 by insertion into a bore defined in handle 60 and tightening of two set screws 62 also on the handle 60.

The handle 60 is cylindrical in shape with a proximal end 61 and a distal end 65. A bore 63, shown in FIG. 7, which is dimensioned to accommodate the proximal end of the needle 55, runs from the proximal end 61 of the handle 61 toward the distal end 65 of the handle 60. Two threaded holes 64, seen in FIG. 7, dimensioned to accommodate set screws 62, run perpendicular from the bore 63 to and through the surface of the handle 60. Two set screws 62 are tightened in the threaded holes 64, against the portion of the needle 51 that is within the bore 63. The surface of the handle 60 preferably is knurled.

Figure 5A:
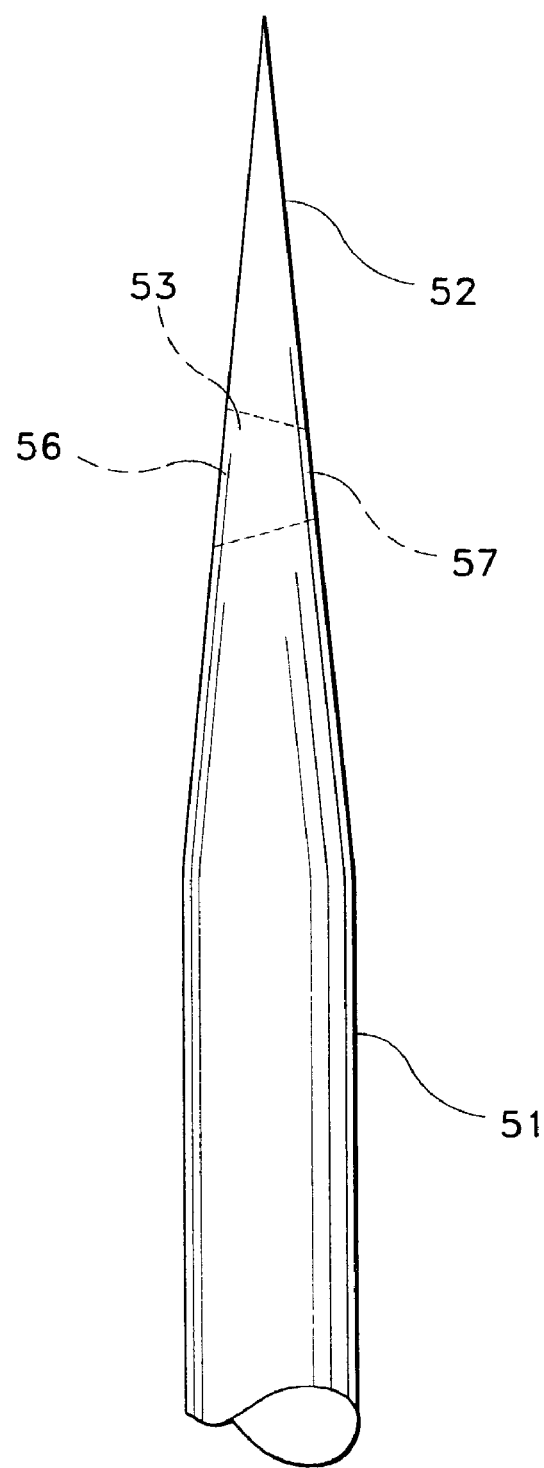
FIG. 5A is a fragmented, detail view of the tip of the trocar needle of FIG. 5.

FIG. 5A presents a sectional side view of the tip 52 of the trocar needle 50. The eyelet 53 is shown in phantom lines. The opening of the eyelet 53 is larger on one side 56 of the needle 51 than on the diametrically opposed side 57, to help a surgeon to determine, via a laparoscopic opening, on which side of the needle 51 the end of the suture is located.

Figure 6:
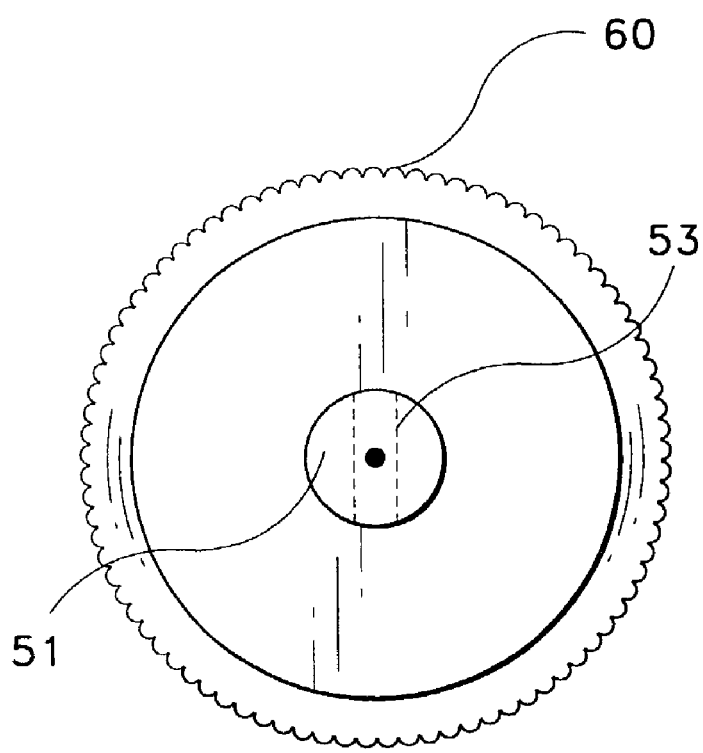
FIG. 6 is a top end view of the trocar needle and handle of FIG. 5 according to the present invention.
Figure 7:
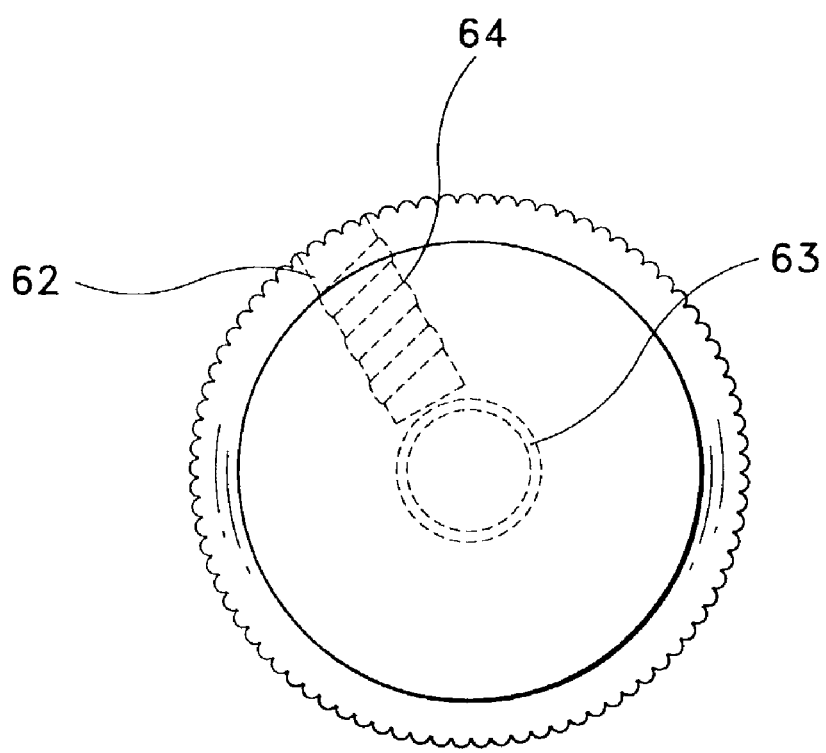
FIG. 7 is a bottom end view of the trocar needle and handle of FIG. 5 according to the present invention.

FIG. 6 presents a top end view of the trocar needle 50. The eyelet 53 of the needle 51 is shown in phantom lines. FIG. 7 presents a bottom end view of the trocar needle 50. The bore 63 in the handle 60 and the threaded holes 64 are shown in phantom lines.

Figure 8A:
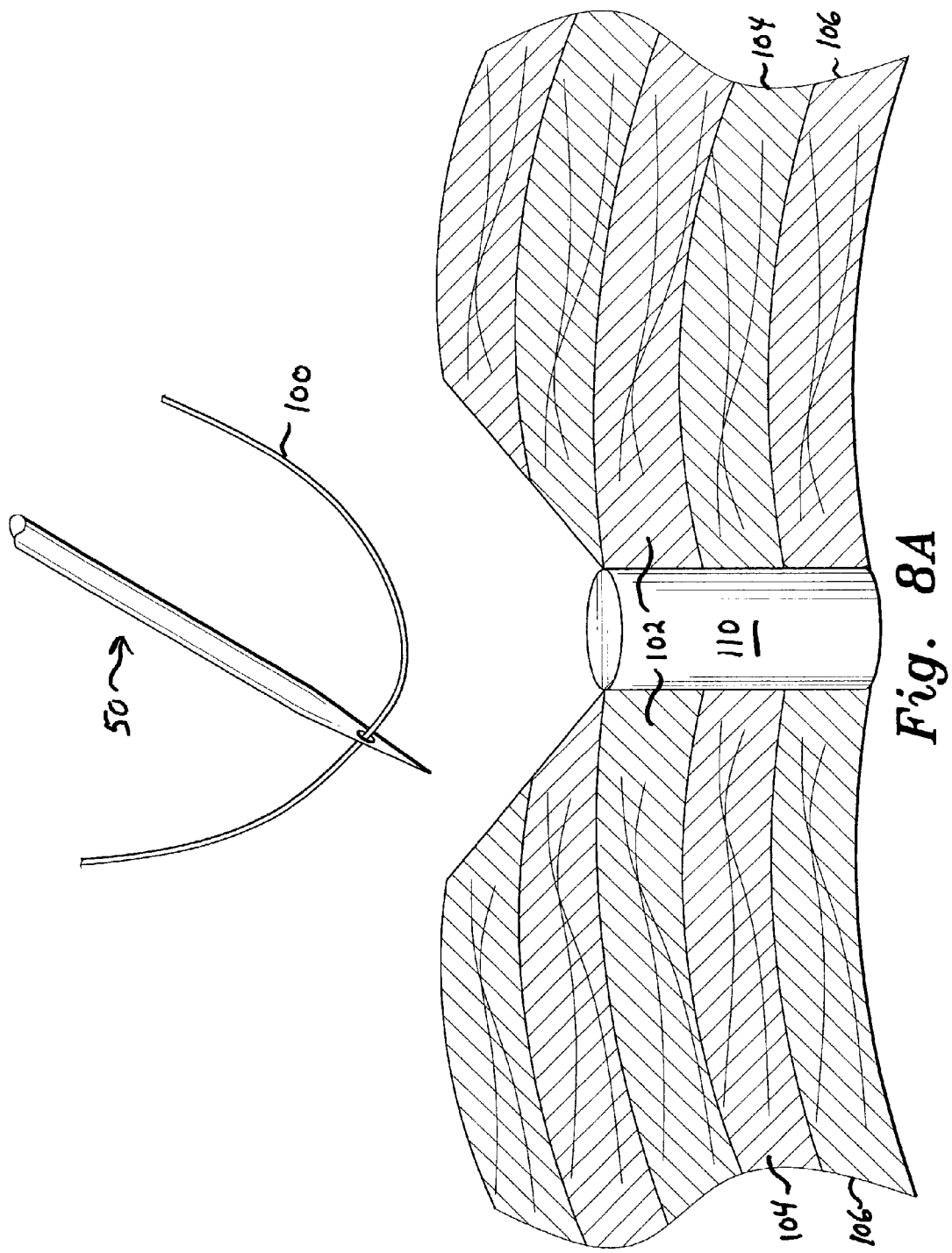
Figure 8D:
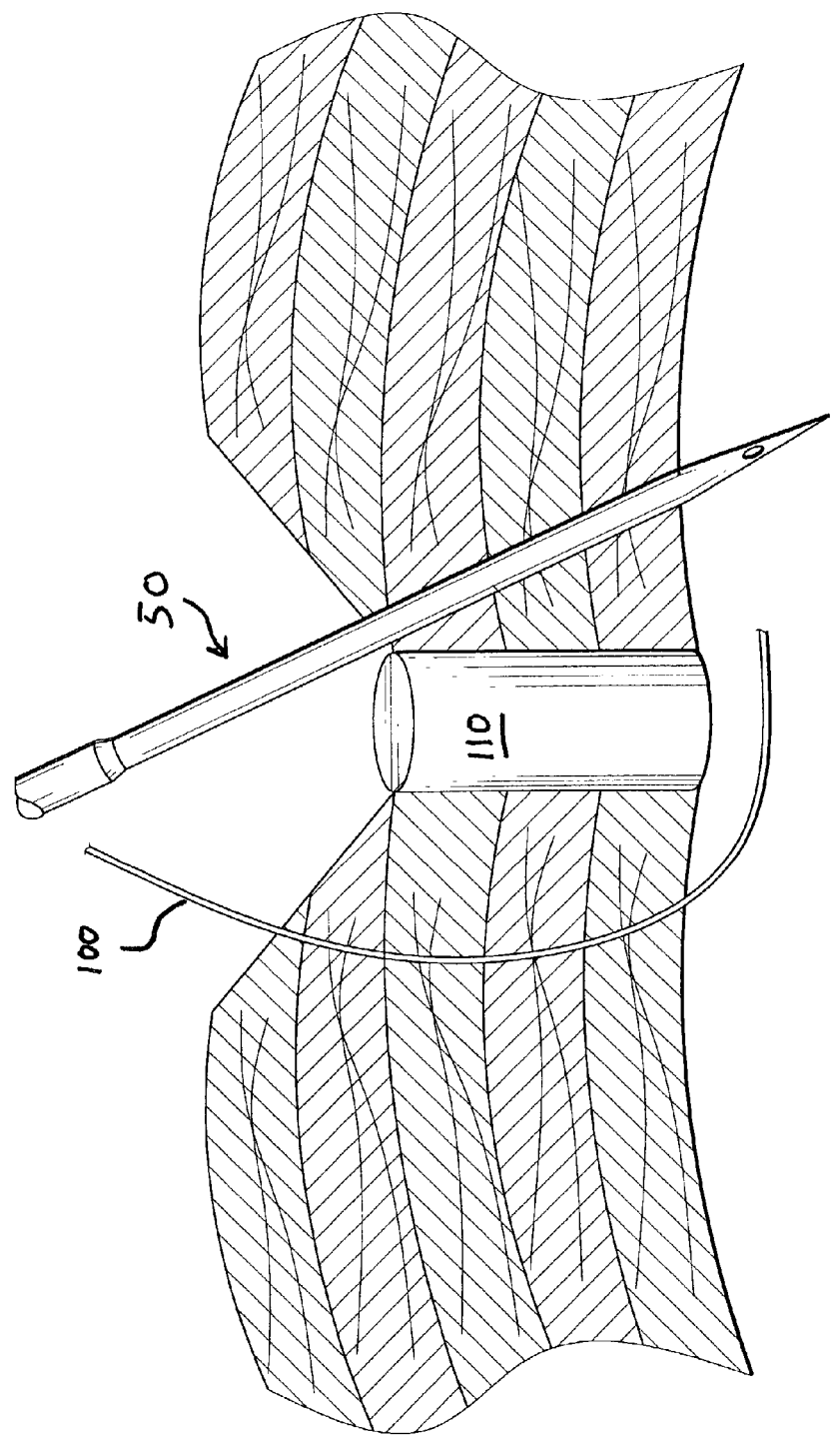
Figure 8G:
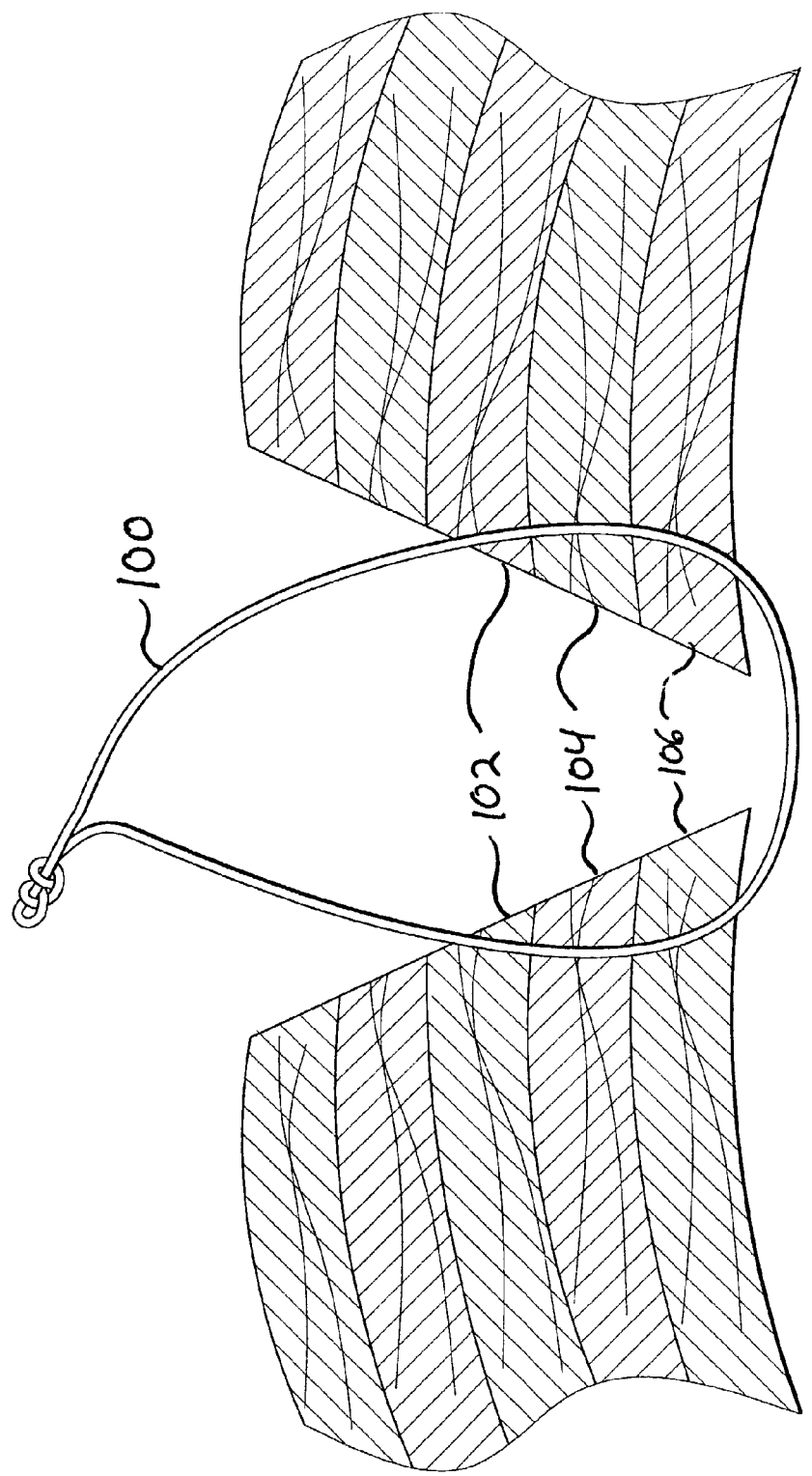

FIGS. 8A through 8G diagrammatically illustrate suturing of a laparoscopic incision with the trocar needle 50. As shown in FIG. 8A, the needle 50 is threaded with suture 100 and positioned over the fascia layer 102 on one side of the incision while the cannula 110 is still in place. The device is then inserted through the fascia 102, muscle 104 and peritoneal 106 layers at approximately a forty-five degree angle, as shown in FIG. 8B. Dolphin forceps 112 are used to hold the suture 100 in place as the needle 50 is withdrawn from the tissue, as seen in FIG. 8C. The needle 50, without suture, is then inserted through the tissue on the other side of the incision, as shown in FIG. 8D (the forceps being omitted in FIG. 8D for clarity), and the suture 100 is threaded into the eyelet 53 by manipulating the suture material 100 in the incision using forceps 112, as shown in FIG. 8E. After both the needle 50 and the cannula 110 are withdrawn from the tissue, the two ends of the suture 100 are knotted, as shown in FIGS. 8F and 8G.

Both trocar needles 11 and 51 are preferably made from stainless steel. The handles 10 and 60 may be made from aluminum.

It is to be understood that the present invention is not limited to the embodiments described above, but encompasses any and all embodiments within the scope of the following claims.

I claim:

1. A trocar needle and handle for suturing incisions, comprising:
    an elongate cylindrical handle;
    an elongate, straight, cylindrical needle shaft extending from an end of said handle, the needle shaft terminating in an end formed to a sharp, straight, pointed tip;
    said elongate cylindrical handle, needle shaft and tip being aligned along an axis and in a substantially straight line;
    said tip having an eyelet defined therein;
    said eyelet comprising a bore extending transversely through said tip;
    said bore having an opening on one side of said tip that is larger than an opening of said bore on a diametrically opposed side of said tip;
    whereby the different size bore openings are designed for identification, through a laparoscope, by a surgeon suturing an incision.

2. The trocar needle and handle according to claim 1, wherein the trocar needle is constructed of material that is capable of being easily and repeatedly sterilized.

3. The trocar needle and handle according to claim 1, wherein the handle is constructed of aluminum and the needle shaft is constructed of stainless steel.

4. The trocar needle and handle according to claim 1, wherein the handle has a bore defined axially therein, said bore in said handle adapted to receive said needle shaft, the handle further having two threaded holes defined transversely and extending to the bore in said handle, the trocar needle and handle further comprising a set screw extending through each of said threaded holes into the bore in said handle and bearing against said needle shaft in order to attach said needle shaft to said handle.

5. The trocar needle and handle according to claim 1, wherein the needle shaft has a first section proximal to said handle and a second section proximal to the tip, the needle shaft having a shoulder defined therein dividing the first section from the second section, the first section having a greater diameter than the second section, said shoulder forming a stop to prevent the needle shaft from being inserted too deep into tissue.

* * * * *